United States Patent
Wang et al.

(10) Patent No.: US 9,279,888 B2
(45) Date of Patent: Mar. 8, 2016

(54) SYSTEM FOR ONLINE/OFFLINE SINGLES-PAIRING WITH KEEPING/REJECTING MULTI-COINCIDENCES FOR POSITRON EMISSION TOMOGRAPHY

(75) Inventors: Wenli Wang, Manor, NY (US); Ognian Ivanov, Lake Zurich, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 880 days.

(21) Appl. No.: 13/156,035

(22) Filed: Jun. 8, 2011

(65) Prior Publication Data

US 2012/0316837 A1  Dec. 13, 2012

(51) Int. Cl.
G06F 17/40 (2006.01)
G01T 1/17 (2006.01)
A61B 6/03 (2006.01)

(52) U.S. Cl.
CPC .. *G01T 1/17* (2013.01); *A61B 6/037* (2013.01)

(58) Field of Classification Search
CPC .................................. G01T 1/17; A61B 6/037
USPC .......................................... 702/187; 250/362
See application file for complete search history.

(56) References Cited

U.S. PATENT DOCUMENTS

| 8,084,741 | B2 | 12/2011 | Gagnon et al. | |
| 2002/0121603 | A1* | 9/2002 | Wong et al. | 250/363.09 |
| 2003/0062482 | A1* | 4/2003 | Williams et al. | 250/363.03 |
| 2007/0023669 | A1* | 2/2007 | Hefetz et al. | |
| 2009/0127467 | A1* | 5/2009 | Frach | 250/363.03 |
| 2010/0084559 | A1* | 4/2010 | Aykac et al. | |
| 2010/0264320 | A1* | 10/2010 | Takayama et al. | |

FOREIGN PATENT DOCUMENTS

JP  2011-75552  4/2011

OTHER PUBLICATIONS

Josep F. Oliver et al., "Comparison of Coincidence Identification Techniques for High Resolution PET", 2008 IEEE uclear Science Symposium Conference Record, 2008, pp. 4732-4735.
M. -A. Tétrault et al., "Real Time Coincidence Detection Engine for High Count Rate Timestamp Based PET", IEEE Transactions on Nuclear Science, vol. 57, No. 1, Feb. 2010, pp. 117-124.

(Continued)

*Primary Examiner* — Mischita Henson
*Assistant Examiner* — Stephanie Bloss
(74) *Attorney, Agent, or Firm* — Oblon, McClelland, Maier & Neustadt, L.L.P.

(57) ABSTRACT

A method of processing, by a processor of a computer, positron emission tomography (PET) information obtained from a PET detector, including the steps of obtaining a singles event list that includes a plurality of single event entries, each entry corresponding to a single event detected by the PET detector and including a timestamp, energy information, and crystal position information; and determining, based on the timestamp and the crystal position information of each entry and a predetermined coincidence time period, all event pairs within the plurality of single event entries, each event pair consisting of two single events whose respective timestamps differ by less than the predetermined coincidence time period, wherein the determining step determines that an event pair exists when at least two, but no more than k, single events are found within a given time window, wherein k is an integer value greater than or equal to two.

16 Claims, 4 Drawing Sheets

(56) References Cited

OTHER PUBLICATIONS

Chao Wang et al., "A Low-Cost Coincidence System with Capability of Multiples Coincidence for High Count-Rate TOF or Non-TOF PET Cameras Using Hybrid Method Combining AND-logic and Time-mark Technology", 2009 IEEE Nuclear Science Symposium Conference Record, 2009, pp. 3633-3638.

International Search Report issued Jul. 17, 2012 in Application No. PCT/JP2012/064841 (With English Translation of Category of Cited Documents).

Yuxuan Zhang, et al., "The Systematic Errors in the Random Coincidence Estimation Using a Delayed Window", 2009 IEEE Nuclear Science Symposium Conference Record, Oct. 24, 2009, pp. 3897-3899.

* cited by examiner

SYSTEM FOR ONLINE/OFFLINE SINGLES-PAIRING WITH KEEPING/REJECTING MULTI-COINCIDENCES FOR POSITRON EMISSION TOMOGRAPHY

CROSS-REFERENCE TO RELATED APPLICATION

The present application is related to application Ser. No. 12/571,562, filed Oct. 1, 2009, the contents of which are incorporated herein be reference.

FIELD

Embodiments described herein relate generally to a system for singles pairing in positron emission tomography.

BACKGROUND

The use of positron emission tomography (PET) is growing in the field of medical imaging. In PET imaging, a radiopharmaceutical agent is introduced into the object to be imaged via injection, inhalation, or ingestion. After administration of the radiopharmaceutical, the physical and bio-molecular properties of the agent will cause it to concentrate at specific locations in the human body. The actual spatial distribution of the agent, the intensity of the region of accumulation of the agent, and the kinetics of the process from administration to eventually elimination are all factors that may have clinical significance. During this process, a positron emitter attached to the radiopharmaceutical agent will emit positrons according to the physical properties of the isotope, such as half-life, branching ratio, etc.

The radionuclide emits positrons, and when an emitted positron collides with an electron, an annihilation event occurs, wherein the positron and electron are destroyed. Most of the time an annihilation event produces two 511 keV gamma rays traveling at substantially 180 degrees apart.

By detecting the two gamma rays, and drawing a line between their locations, i.e., the line-of-response (LOR), one can retrieve the likely location of the original disintegration. While this process will only identify a line of possible interaction, by accumulating a large number of those lines, and through a tomographic reconstruction process, the original distribution can be estimated. In addition to the location of the two scintillation events, if accurate timing (within few hundred picoseconds) is available, a time-of-flight (ToF) calculation can add more information regarding the likely position of the event along the line. The collection of a large number of events creates the necessary information for an image of an object to be estimated through tomographic reconstruction. Two detected events occurring at substantially the same time at corresponding detector elements form a line-of-response that can be histogrammed according to their geometric attributes to define projections, or sinograms to be reconstructed. Direct reconstruction of the LORs in list-mode format without histogramming is also possible, which is usually done in the TOF case.

In PET, scintillation crystals with related detector electronics are used to detect these emitted photons, and then a 3D radioisotope distribution of the organism can be obtained. In PET, the initial data detected from scintillation crystals are single events. A pairing scheme is needed to connect two single events, whose arrival time difference is within a coincidence timing window, into coincidence events. In the coincidence events, which we call "prompts," not all paired events are from the same annihilation points, which we call "true coincidences." A fraction of them are due to the accidental pairing of two singles from two different annihilation points, which we call "randoms" or "accidental coincidences."

In conventional systems, single pairing is performed using a hardware implementation of pairing in and-logic and/or with ASIC chips, while multi-coincidence is rejected for most clinical PET scanners. Further, in conventional systems, the transaxial imaging FOV is determined coarsely by detector block/module pairs.

However, conventional pairing methods have several disadvantages, including: (1) little flexibility when there is need to change pairing parameters or schemes; (2) the detector block/module pair only defines a coarse transaxial imaging FOV, and there is a need to further trim down the excess imaging FOV using other methods in later data processing; (3) there is no direct evaluation or comparison of hardware pairing with "gold standard" pairing results obtained using, e.g., GATE simulated data, and there is a need to write separate pairing code to check results with GATE simulated data; (4) a hardware implementation of pairing does not allow the same circuitry to be used for different scanner geometries and variants; thus hardware reuse between different systems is limited or non-existent, which results in high engineering development and material cost; (5) using specialized hardware (and-logic and/or ASIC chips) for pairing increases the risk of having to re-spin ASICs or boards during the development and maintenance phases if defects and/or improvements are needed, which results in a significant cost increase; and (6) the specialized hardware used for pairing cannot be used by the scanner system to perform any other functions during the periods when the pairing function is idle.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
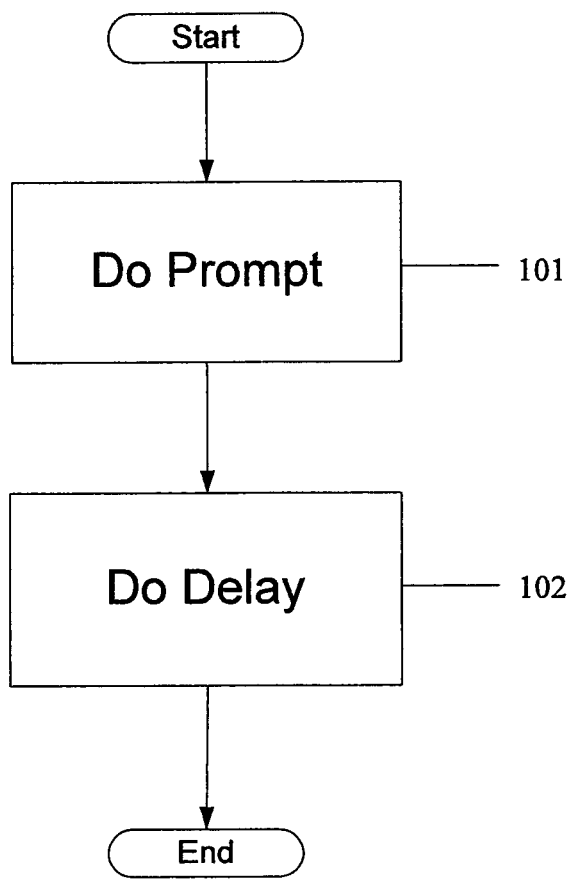
FIG. 1 illustrates a flowchart of a method of event pairing according to embodiments disclosed herein.

Embodiments disclosed herein include a method of processing, by a processor of a computer, positron emission tomography (PET) information obtained from a PET detector, the method comprising: (1) obtaining a singles event list that includes a plurality of single event entries, each entry corresponding to a single event detected by the PET detector and including a timestamp, energy information, and crystal position information; and (2) determining, based on the timestamp and the crystal position information of each entry of the plurality of single event entries and a predetermined coincidence time period, all event pairs within the plurality of single event entries, each event pair consisting of two single events whose respective timestamps differ by less than the predetermined coincidence time period, wherein the determining step determines that an event pair exists when at least two, but no more than k, single events are found within a given time window having a period equal to the predetermined coincidence time period, wherein k is an integer value greater than or equal to two.

In another embodiment, k=2 and the determining step comprises determining that the event pair exists when exactly two single events are found within the given time window, thereby rejecting multi-coincidence.

In an alternative embodiment, k>2 and the determining step comprises determining that the event pair exists when at least two but less than k single events are found within the given time window, thereby accepting some multi-coincidence.

In an alternative embodiment, the determining step comprises accepting all event pairs that are within the given time window, thereby accepting all multi-coincidence.

In another embodiment, the method further comprises filtering the singles event list by removing those entries of the plurality of entries having respective energy information that is outside a predetermined energy window.

In another embodiment, the obtaining step comprises reading the singles event list from a memory, wherein the singles event list was transmitted to the memory from the PET detector for off-line processing.

In particular, embodiments disclosed herein relate to pairing algorithms to pair singles into coincidences and to estimate the number of randoms in the prompts. In particular, embodiments disclosed herein provide an on-line (FPGA) and an off-line (CPU) singles-pairing algorithm, wherein multi-coincidence can be all or partially accepted depending on the number of singles falling in the coincidence window. The pairing algorithms assume that the singles data from all detector modules are mixed together and ordered in an ascending-time order. Alternative embodiments are applicable to random coincidence estimation using a delayed-coincidence window.

The pairing algorithms also post-filter coincidence events by checking their spatial position. For any paired event, the line-of-response (LOR) is accepted if it is within a preselected transverse reconstruction field-of-view (FOV). The FOV is determined by a look-up-table indexed by the transverse crystal ID of the LOR.

FIG. 1 illustrates an overall pairing algorithm according to embodiments described herein. In particular, as shown in FIG. 1, a prompt pairing process is performed in step 101, followed by a delay pairing process in step 102. The prompt pairing process is illustrated in FIG. 2, while the delay pairing process is illustrated in FIG. 3, both of which are discussed in more detail below.

"Do Prompt" Process

Figure 2:
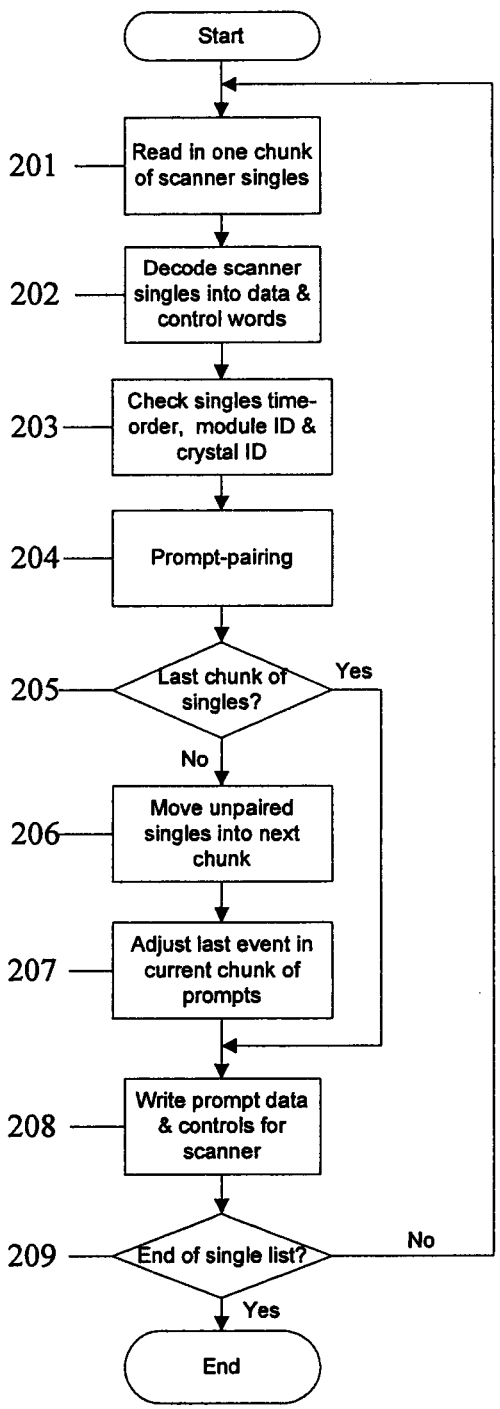
FIG. 2 illustrates a flowchart of a method of prompt pairing according to an embodiment disclosed herein.
Figure 3:
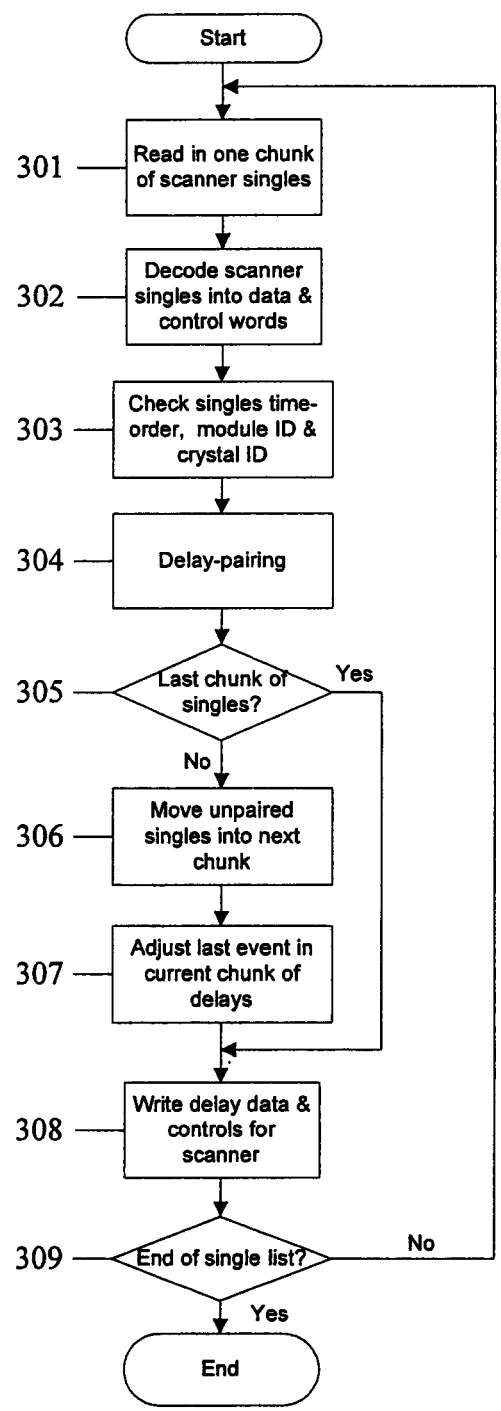
FIG. 3 illustrates a flowchart of a method of delay pairing according to an embodiment disclosed herein.

FIG. 2 illustrates the prompt pairing process "Do Prompt" shown in step 101 of FIG. 1. As discussed above, the prompt pairing process assumes that the singles data from all detector modules are mixed together and ordered and arranged in a list in an ascending-time order. Moreover, each single event includes various data relating to the event, including (1) a fine time stamp with a predetermined time resolution, e.g., 16 ps, (2) crystal position information, including, e.g., a module index, a crystal index with the module, and a crystal layer value, (3) an energy value of the event, e.g., in ⅛ keV increments, and (4) a trigger zone identifier. Other or additional information can also be included within the single event data without departing from the scope of the embodiments disclosed herein. Further, other time or energy resolutions of the single event data can be used.

Moreover, in the list of single events, there are control words, such as coarse time stamps, which when combined with the fine time stamp for each single event, gives the exact arrival time for each single event. Further, in the list of single events, there can be other non-PET event control words, e.g., patient table position, respiratory/cardiac gating information, etc.

In step 201, a chunk of single events is read from the event list. The number of events in the chunk is a predetermined, adjustable value.

In step 202, the information in the read singles events in the chunk is decoded into the various data fields.

In step 203, the time, module index, and crystal index are checked to make sure that the times of the single events are in ascending order, and that the module and crystal indices are within the correct range.

In step 204, a prompt-pairing algorithm is executed. In particular, as described below, a range of different prompt-pairing algorithms can be executed. For example, in one embodiment, multi-coincidence is rejected, while in another, multi-coincidence is accepted. In a third embodiment, an adjustable parameter controls the amount of multi-coincidence that is accepted. Pseudo-code for each of the three example algorithms is set forth below.

Prompt-Pairing Algorithm (Keeping all Multi-Coincidence):

1. Read in a chunk of singles file with size n
2. Initialize two singles indices: i=0, j=1
3. While (i < n−1) do following
   a. Read in single event i's time $t_i$ (coarse time + fine time) and transverse crystal number $x_i$
   b. While (j < n) do following
      (a) Read in single event j's time $t_j$ (coarse time + fine time) and transverse crystal number $x_j$
      (b) Compute dt=$t_j$−$t_i$
      (c) If (dt < coinWin) then
         (i) If ($x_i$ & $x_j$ within reconFOV) then found a prompt pair
         (ii) j++
      (d) Else goto step 3.c
   c. i++, j=i+1

Prompt-Pairing Algorithm (Keeping Up to k Multi-Coincidence):

1. Read in a chunk of singles file with size n
2. Initialize two singles indices: i=0, j=1
3. While (i < n−1) do following
   a. Read in single event i's time $t_i$ (coarse time + fine time) and transverse crystal number $x_i$
   b. Set nSingInCoin=1
   c. While (j < n) do following
      (a) Read in single event j's time $t_j$ (coarse time + fine time) and transverse crystal number $x_j$
      (b) Compute dt=$t_j$−$t_i$
      (c) If (dt < coinWin) then nSingInCoin++, j++
      (d) Else goto step 3.d
   d. If (k>=nSingInCoin>=2 and $x_i$ & $x_{ib}$ within reconFOV) then found a prompt pairs between {i, ib}, where ib=j−nSingInCoin+1, ..., j−1.
   e. i++, j=i+1

Prompt-Pairing Algorithm (Rejecting Multi-Coincidence):

1. Read in a chunk of singles file with size n
2. Initialize two singles indices: i=0, j=1
3. While (i < n−1) do following
   a. Read in single event i's time $t_i$ (coarse time + fine time) and transverse crystal number $x_i$
   b. Set nSingInCoin=1
   c. While (j < n) do following
      (a) Read in single event j's time $t_j$ (coarse time + fine time) and transverse crystal number $x_j$
      (b) Compute dt=$t_j$−$t_i$ -continued (c) If (dt < coinWin) then nSingInCoin++, j++
    (d) Else goto step 3.d
  d. If (nSingInCoin=2 and $x_i$ & $x_{j-1}$ within reconFOV) then found a prompt pair
  e. i+=nSingInCoin, j=i+1

As illustrated in the pseudo-code shown above, each algorithm operates on a chunk of n single events, wherein n is a positive integer. Further, each algorithm includes a double-loop over the n events in the chunk and, for two given events in the chunk, computes the difference in time (dt) between the two events, and checks whether dt is within a predetermined coincidence time window (coinWin). The first algorithm accepts all multi-coincidence. The second two algorithms listed above, which reject or partially reject multi-coincidence, also keep track of the number of coincidences (nSingInCoin) for a given single event. The third algorithm, which completely rejects multi-coincidence, requires nSingInCoin to be exactly two, while the second algorithm, which partially rejects multi-coincidence, requires nSingInCoin to be at least two, but less than or equal to an integer k, wherein k is adjustable. By adjusting the parameter k, the amount of multi-coincidence that is accepted or rejected can be controlled.

The result of step 204, in which a prompt pairing algorithm is executed, is the generation of prompt pairs. As each prompt pair is determined, information regarding the pair is stored in a memory. The information regarding the prompt pair includes, for example, the crystal position of the first event of the pair, the crystal position of the second event of the pair, the energy of the first event, the energy of the second event, and a timestamp. Each crystal position can include a transverse crystal position (with respect to all detector modules), an axial crystal position, and DOI (crystal layer) information. Moreover, the timestamp can be the time-of-flight difference between the first and second events of the pair. Other or additional information can also be included within the information regarding a prompt pair without departing from the scope of the embodiments disclosed herein.

In step 205, a check is made as to whether there are more single events to be processed. If "yes", the process skips to step 208. If "no", the process proceeds to step 206.

In step 206, singles that remain unpaired are moved to a next chunk of singles data for future processing.

In step 207, the last event in the current chunk of events is adjusted to allow single events in the current chunk to be paired with single events in the next chunk so that no prompts will be missed between data chunks.

In step 208, prompt data and controls (such as coarse time stamp, patient table position, and respiratory/cardiac gating information) for the scanner are written.

In step 209, a check is made as to whether the end of the event list has been reached. If "no", the process proceeds back to step 201 in which another chunk of single events is read from the list. If "yes", the "Do Prompt" process ends.

"Do Delay" Process

FIG. 3 illustrates the delay pairing process "Do Delay" shown in step 102 of FIG. 1. The process shown in FIG. 3 is similar to the process shown in FIG. 2 except for the delay pairing algorithm in step 304. The delay pairing process assumes that the singles data from all detector modules are mixed together and ordered and arranged in a list in an ascending-time order. As discussed above, each single event includes various data relating to the event, including (1) a fine time stamp with a resolution of, e.g., 16 ps, (2) crystal position information, including, e.g., a module index, a crystal index with the module, and a crystal layer value, (3) an energy value of the event, e.g., in ⅙ keV increments, and (4) a trigger zone identifier. Other or additional information can also be included within the single event data without departing from the scope of the embodiments disclosed herein. Further, other time or energy resolutions of the single event data can be used.

In step 301, a chunk of single events is read from the event list. The number of events in the chunk is a predetermined, adjustable value.

In step 302, the information in the read singles events in the chunk is decoded into the various data fields.

In step 303, the time, module index, and crystal index are checked to make sure that the times of the single events are in ascending order, and the module and crystal indices are within the correct range.

In step 304, a delay-pairing algorithm is executed. In particular, as described below, a range of different delay-pairing algorithms can be executed. For example, in one embodiment, multi-coincidence is rejected, while in another, multi-coincidence is accepted. In a third embodiment, an adjustable parameter controls the amount of multi-coincidence that is accepted. Pseudo-code for each of the three example algorithms is set forth below.

Delay-Pairing Algorithm (Keeping all Multi-Coincidence):

1. Read in a chunk of singles file with size n
2. Initialize two singles indices: i=0, j=1
3. While (i < n−1) do following
  a. Read in single event i's time $t_i$ (coarse time + fine time) and transverse crystal number $x_i$
  b. While (j < n) do following
    (a) Read in single event j's time $t_j$ (coarse time + fine time) and transverse crystal number $x_j$
    (b) Compute dt=$t_j$−$t_i$−delayWin
    (c) If (0<dt< coinWin) then
      (i) If ($x_i$ & $x_j$ within reconFOV) then found a delay pair
      (ii) j++
    (d) Else if dt<=0 then j++ else goto step 3.c
  c. i++, j=i+1

Delay-Pairing Algorithm (Keeping Up to k Multi-Coincidence):

1. Read in a chunk of singles file with size n
2. Initialize two singles indices: i=0, j=1
3. While (i < n−1) do following
  a. Read in single event i's time $t_i$ (coarse time + fine time) and transverse crystal number $x_i$
  b. Set nSingInCoin=1
  c. While (j < n) do following
    (a) Read in single event j's time $t_j$ (coarse time + fine time) and transverse crystal number $x_j$
    (b) Compute dt=$t_j$−$t_i$
    (c) If (dt < coinWin) then nSingInCoin++, j++
    (d) Else goto step 3.d
  d. If (k>=nSingInCoin>=2 and $x_i$ & $x_{ib}$ within reconFOV) then found a event pair between {i, ib}, where ib=j−nSingInCoin+1, ..., j−1.
  e. i++, j=i+1

Delay-Pairing Algorithm (Rejecting Multi-Coincidence):

1. Read in a chunk of singles file with size n
2. Initialize two singles indices: i=0, j=1
3. While (i < n−1) do following
  a. Read in single event i's time $t_i$ (coarse time + fine time) and transverse crystal number $x_i$
  b. Set nSingInCoin=1
  c. While (j < n) do following (a) Read in single event j's time $t_j$ (coarse time + fine time) and transverse crystal number $x_j$
(b) Compute dt=$t_j$-$t_i$-delayWin
(c) If (0<dt< coinWin) then nSingInCoin++, j++
(d) Else if dt<=0 then j++ else goto step 3.d
d. If (nSingInCoin=2 and $x_i$ & $x_{j-1}$ within reconFOV) then found a delay pair
e. i+=nSingInCoin, j=i+1

As illustrated in the pseudo-code shown above, each algorithm operates on a chunk of n single events, wherein n is a positive integer. Further, each algorithm includes a double-loop over the n events in the chunk and, for two given events in the chunk, computes dt as the difference in time between the two events minus the delay window (delayWin), and checks whether dt is within a predetermined coincidence time window (coinWin). The first algorithm accepts all multi-coincidence. The second two algorithms listed above, which reject or partially reject multi-coincidence, also keep track of the number of coincidences (nSingInCoin) for a given single event. The third algorithm, which completely rejects multi-coincidence, requires nSingInCoin to be exactly two, while the second algorithm, which partially rejects multi-coincidence, requires nSingInCoin to be at least two, but less than or equal to an integer k, which is adjustable. By adjusting the parameter k, the amount of multi-coincidence that is accepted or rejected can be controlled.

The result of step 304, in which the delay pairing algorithm is executed, is the generation of delay pairs. As each delay pair is determined, information regarding the pair is stored in a memory. The information regarding the delay pair includes, for example, the crystal position of the first event of the pair, the crystal position of the second event of the pair, the energy of the first event, the energy of the second event, and a timestamp. Each crystal position can include a transverse crystal position (with respect to all detector modules), an axial crystal position, and DOI (crystal layer) information. Moreover, the timestamp can be the time-of-flight difference between the first and second events of the pair. Other or additional information can also be included within the information regarding a delay pair without departing from the scope of the embodiments disclosed herein.

In step 305, a check is made as to whether there are more single events to be processed. If "yes", the process skips to step 308. If "no", the process proceeds to step 306.

In step 306, singles that remain unpaired are moved to a next chunk of singles data for future processing.

In step 307, the last event in the current chunk of delays is adjusted to allow single events in the current chunk to be paired with the single events in the next chunk so that no delays will be missed between data chunks.

In step 308, delay data and controls for the scanner are written (such as coarse time stamp, patient table position, and respiratory/cardiac gating information).

In step 309, a check is made as to whether the end of the event list has been reached. If "no", the process proceeds back to step 301 in which another chunk of single events is read from the list. If "yes", the "Do Delay" process ends.

In one embodiment, the particular pairing algorithm executed in the "Do Prompt" step is analogous to the particular pairing algorithm executed in the "Do Delay" step. For example, if a prompt pairing algorithm in which multi-coincidence is completely rejected is chosen, a delay pairing algorithm in which multi-coincidence is completely rejected is also chosen. Also, if a prompt pairing algorithm in which up to k multi-coincidence is accepted is chosen, a delay pairing algorithm in which up to k multi-coincidence is accepted is also chosen, wherein k has the same value in both algorithms.

Figure 4:
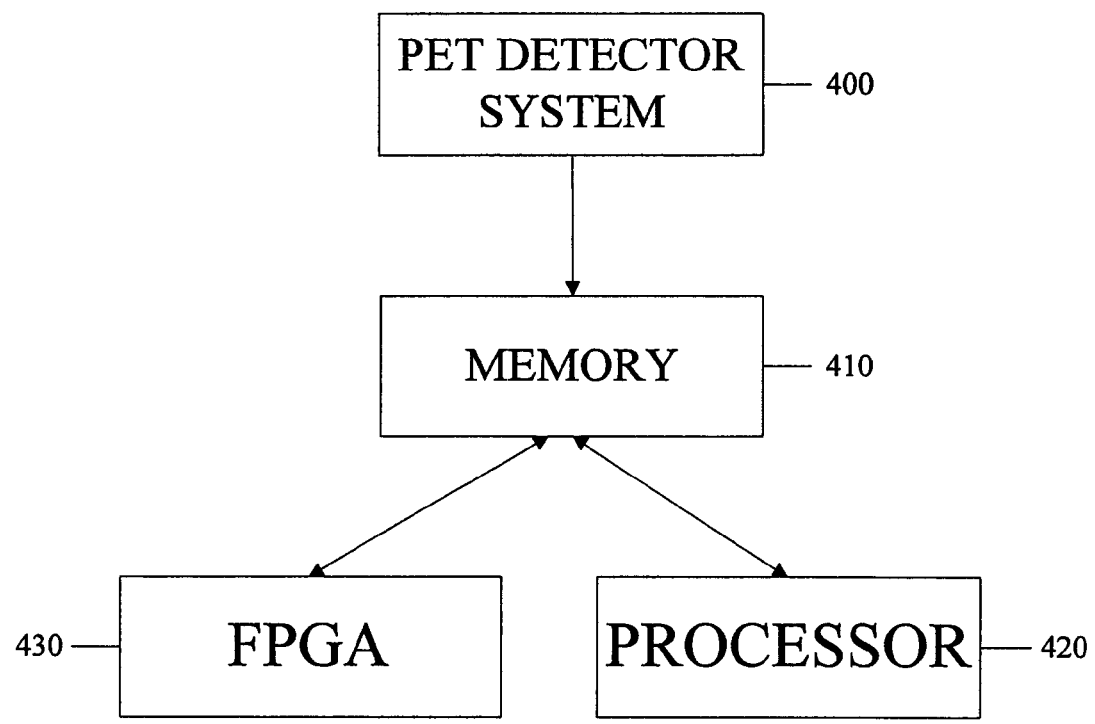
FIG. 4 illustrates a system according to one embodiment.

FIG. 4 illustrates a system for processing positron emission tomography information obtained from a PET detector. The system includes a PET detector system 400 that receives PET event information for plurality of single PET events, the PET event information including energy information and crystal position information of the single PET event. The PET detector system 400 generates a singles event list that includes a plurality of entries, each entry including a time stamp, energy information, and crystal position information of the single event and transmits the generated event list to the memory 410 for off-line processing. The transmission of the singles event list can be via a network and the memory 410 can be part of an apparatus that includes a computer processor 420 or an FPGA 430. Alternatively, the memory unit 410 can be separate from the computer 420.

Once the singles event list is stored in the memory 410, it can be read as needed by the processor 420 for prompt pairing and delay pairing using the algorithms described above. As discussed above, the processor 420 generates event pairs, which can be stored in the memory 410, or alternatively, in another memory (not shown). Reconstruction processing can then be performed by the processor 420 or another processor using the paired event data stored in the memory 410.

Alternatively, the prompt pairing and the delay pairing algorithms can be implemented by an FPGA 430 using the singles event list stored in memory 410.

The embodiments described herein provide several advantages. For example, the embodiments have great flexibility in choosing different pairing schemes for different imaging tasks.

Further, the embodiments disclosed herein provide for a flexible software implementation by CPU (off-line) or FPGA (on-line), unlike less flexible hardware implementations using AND-logic or custom chips, as in most commercial clinical scanners, For example, the disclosed embodiments allow for accepting any number of singles in multi-coincidence or partially accepting multi-coincidence, e.g., accepting two or three singles in multi-coincidence, but rejecting four or more singles in multi-coincidence.

Further, in the embodiment in which the pairing is implemented in programmable logic (FPGA), the same circuitry can be used for different scanner geometries and variants by reconfiguring only the FPGA(s), i.e., the hardware is highly reusable between different systems, which results in low engineering development and material cost.

Further, the use of generic hardware of the programmable logic (FPGA) for pairing minimizes the risk of having to re-spin hardware during the development and maintenance phases if defects and/or improvements are needed, which results in low cost development and maintenance. In addition, the generic hardware of the programmable logic (FPGA) used for pairing can be used by the PET detector system to perform other functions during the periods when the pairing function is idle, which may ultimately lower the system cost.

Further, the embodiments disclosed herein allow for precise and accurate transaxial image FOV selection.

In the embodiments disclosed herein, the pairing algorithm in which all multi-coincidence is accepted is more accurate and optimal over most pairing schemes used in commercial clinical scanner. In particular, accepting all multi-coincidence accurately estimates the amount of randoms in the prompt coincidence using a delay-window at all singles-count-rate ranges. Further, accepting all multi-coincidence achieves the highest noise-equivalent-count (NEC) rate over other pairing schemes in data acquisition. Moreover, accepting all multi-coincidence achieves the best lesion detectability in reconstructed images.

The singles pairing processing described above can be implemented using a computer system or programmable logic (FPGA). A computer system upon which various components of the embodiments disclosed herein may be implemented includes a bus or other communication mechanism for communicating information, and a processor coupled with the bus for processing the information. The computer system also includes a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by processor. In addition, the main memory may be used for storing temporary variables or other intermediate information during the execution of instructions by the processor. The computer system further includes a read only memory (ROM) or other static storage device (e.g., programmable ROM (PROM), erasable PROM (EPROM), and electrically erasable PROM (EEPROM)) coupled to the bus for storing static information and instructions for the processor.

The computer system also includes a disk controller coupled to the bus to control one or more storage devices for storing information and instructions, such as a magnetic hard disk, and a removable media drive (e.g., floppy disk drive, read-only compact disc drive, read/write compact disc drive, compact disc jukebox, tape drive, and removable magneto-optical drive). The storage devices may be added to the computer system using an appropriate device interface (e.g., small computer system interface (SCSI), integrated device electronics (IDE), enhanced-IDE (E-IDE), direct memory access (DMA), or ultra-DMA).

The computer system may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system may also include a display controller coupled to the bus to control a display, such as a cathode ray tube (CRT), for displaying information to a computer user. The computer system includes input devices, such as a keyboard and a pointing device, for interacting with a computer user and providing information to the processor. The pointing device, for example, may be a mouse, a trackball, or a pointing stick for communicating direction information and command selections to the processor and for controlling cursor movement on the display. In addition, a printer may provide printed listings of data stored and/or generated by the computer system.

The computer system can perform a portion or all of the processing steps of the embodiments disclosed herein in response to the processor executing one or more sequences of one or more instructions contained in a memory, such as the main memory. Such instructions may be read into the main memory from another computer readable medium, such as a hard disk or a removable media drive. One or more processors in a multi-processing arrangement may also be employed to execute the sequences of instructions contained in main memory. In alternative embodiments, hard-wired circuitry may be used in place of or in combination with software instructions. Thus, embodiments are not limited to any specific combination of hardware circuitry and software.

As stated above, the computer system includes at least one non-transistory computer readable medium or memory for holding instructions programmed according to the teachings of the disclosed embodiments and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read.

Stored on any one or on a combination of computer readable media, the disclosed embodiments includes software for controlling the computer system, for driving a device or devices for implementing the disclosed embodiments, and for enabling the computer system to interact with a human user. Such software may include, but is not limited to, device drivers, operating systems, development tools, and applications software. Such computer readable media further includes the computer program product of the disclosed embodiments for performing all or a portion (if processing is distributed) of the processing performed in implementing the disclosed embodiments.

The computer code devices of the disclosed embodiments may be any interpretable or executable code mechanism, including but not limited to scripts, interpretable programs, dynamic link libraries (DLLs), Java classes, and complete executable programs. Moreover, parts of the processing of the disclosed embodiments may be distributed for better performance, reliability, and/or cost.

The term "computer readable medium" as used herein refers to any medium that participates in providing instructions to the processor for execution. A computer readable medium may take many forms, including but not limited to, non-volatile media, and volatile media. Non-volatile media includes, for example, optical, magnetic disks, and magneto-optical disks, such as the hard disk or the removable media drive. Volatile media includes dynamic memory, such as the main memory.

Various forms of computer readable media may be involved in carrying out one or more sequences of one or more instructions to processor for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system may receive the data on the telephone line and use an infrared transmitter to convert the data to an infrared signal. An infrared detector coupled to the bus can receive the data carried in the infrared signal and place the data on the bus. The bus carries the data to the main memory, from which the processor retrieves and executes the instructions. The instructions received by the main memory may optionally be stored on a storage device either before or after execution by processor.

The computer system also includes a communication interface coupled to the bus. The communication interface provides a two-way data communication coupling to a network link that is connected to, for example, a local area network (LAN), or to another communications network such as the Internet. For example, the communication interface may be a network interface card to attach to any packet switched LAN. As another example, the communication interface may be an asymmetrical digital subscriber line (ADSL) card, an integrated services digital network (ISDN) card or a modem to provide a data communication connection to a corresponding type of communications line. Wireless links may also be implemented. In any such implementation, the communication interface sends and receives electrical, electromagnetic or optical signals that carry digital data streams representing various types of information.

The network link typically provides data communication through one or more networks to other data devices. For example, the network link may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). The signals through the various networks and the signals on the network link and through the communication interface, which carry the digital data to and from the computer system, may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system can transmit and receive data, including program code, through the networks, the network link and the communication interface. Moreover, the network link may provide a connection through a LAN to a mobile device such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of processing, by a processor of a computer, positron emission tomography (PET) information obtained from a PET detector to reconstruct a PET image, the method comprising:
   obtaining a singles event list that includes a plurality of single event entries, each entry corresponding to a single event detected by the PET detector and including a timestamp, energy information, and crystal position information;
   determining, by the processor, based on the timestamp and the crystal position information of each entry of the plurality of single event entries and a predetermined coincidence time period T, all event pairs within the plurality of single event entries, each event pair consisting of two single events whose respective timestamps differ by less than the predetermined coincidence time period T; and
   reconstructing, by the processor, the PET image using the determined event pairs,
   wherein the determining step includes selecting, from the singles event list, an event i having a timestamp $t_i$, detecting all events in the singles event list having a timestamp between $t_i$ and $t_i + T$, and repeating the selecting and detecting steps for each single event in the singles event list to establish a new coincidence time window starting at each $t_i$, and
   the determining step determines that an event pair exists when at least two, but no more than k, single events are found within a given time window having a period equal to the predetermined coincidence time period T, wherein k is an integer value greater than or equal to two.

2. The method of claim 1, wherein k=2 and the determining step comprises determining that the event pair exists when exactly two single events are found within the given time window, thereby rejecting multi-coincidence.

3. The method of claim 1, wherein k>2 and the determining step comprises determining that the event pair exists when at least two but less than k single events are found within the given time window, thereby accepting some multi-coincidence.

4. The method of claim 1, further comprising:
   filtering the singles event list by removing those entries of the plurality of entries having respective energy information that is outside a predetermined energy window.

5. The method of claim 1, wherein the obtaining step comprises:
   reading the singles event list from a memory, wherein the singles event list was transmitted to the memory from the PET detector for off-line processing.

6. The method of claim 1, wherein the determining step comprises determining all event pairs, wherein each event pair consists of two single events whose respective timestamps differ by less than the predetermined coincidence time period T and a line of response formed by the event pair is within D/2 from a center of an imaging field of view, wherein D is a diameter of the imaging field of view.

7. An apparatus for processing positron emission tomography (PET) information obtained from a PET detector to reconstruct a PET image, the apparatus comprising:
   a computer processor configured to
      obtain a singles event list that includes a plurality of single event entries, each entry corresponding to a single event detected by the PET detector and including a timestamp, energy information, and crystal position information;
      determine, based on the timestamp and the crystal position information of each entry of the plurality of single event entries and a predetermined coincidence time period T, all event pairs within the plurality of single event entries, each event pair consisting of two single events whose respective timestamps differ by less than the predetermined coincidence time period T; and
      reconstruct the PET image using the determined event pairs,
   wherein the computer processor is further configured to select, from the singles event list, an event i having a timestamp $t_i$, detect all events in the singles event list having a timestamp between $t_i$ and $t_i + T$, and repeat the selecting and detecting for each single event in the singles event list to establish a new coincidence time window starting at each $t_i$, and
   determine that an event pair exists when at least two, but no more than k, single events are found within a given time window having a period equal to the predetermined coincidence time period T, wherein k is an integer value greater than or equal to two.

8. The apparatus of claim 7, wherein the computer processor is configured to determine that the event pair exists when exactly two single events are found within the given time window, thereby rejecting multi-coincidence.

9. The apparatus of claim 7, wherein the computer processor is configured to determine that the event pair exists when at least two but less than k single events are found within the given time window, wherein k>2, thereby accepting some multi-coincidence.

10. The apparatus of claim 7, wherein the computer processor is further configured to filter the singles event list by removing those entries of the plurality of entries having respective energy information that is outside a predetermined energy window.

11. The apparatus of claim 7, wherein the computer processor is configured to obtain the singles event list by reading the singles event list from a memory, wherein the singles event list was transmitted to the memory from the PET detector for off-line processing.

12. A non-transitory computer-readable storage medium storing a computer program that, when executed by a computer, causes the computer to process positron emission tomography (PET) information obtained from a PET detector to reconstruct a PET image by executing the steps of:

obtaining a singles event list that includes a plurality of single event entries, each entry corresponding to a single event detected by the PET detector and including a timestamp, energy information, and crystal position information;

determining, based on the timestamp and the crystal position information of each entry of the plurality of single event entries and a predetermined coincidence time period T, all event pairs within the plurality of single event entries, each event pair consisting of two single events whose respective timestamps differ by less than the predetermined coincidence time period T; and reconstructing the PET image using the determined event pairs, wherein the determining step includes selecting, from the singles event list, an event i having a timestamp $t_i$, detecting all events in the singles event list having a timestamp between $t_i$ and $t_i+T$, and repeating the selecting and detecting steps for each single event in the singles event list to establish a new coincidence time window starting at each $t_i$, and the determining step determines that an event pair exists when at least two, but no more than k, single events are found within a given time window having a period equal to the predetermined coincidence time period T, wherein k is an integer value greater than or equal to two.

13. The computer-readable medium of claim 12, wherein the k=2 and the determining step comprises determining that the event pair exists when exactly two single events are found within the given time window, thereby rejecting multi-coincidence.

14. The computer-readable medium of claim 12, wherein the k>2 and the determining step comprises determining that the event pair exists when at least two but less than k single events are found within the given time window, thereby accepting some multi-coincidence.

15. The computer-readable medium of claim 12, wherein the program further causes the computer to execute the step of:

filtering the singles event list by removing those entries of the plurality of entries having respective energy information that is outside a predetermined energy window.

16. The computer-readable medium of claim 12, wherein the obtaining step comprises:

reading the singles event list from a memory, wherein the singles event list was transmitted to the memory from the PET detector for off-line processing.

* * * * *